United States Patent [19]

Nardi et al.

[11] Patent Number: 5,520,540
[45] Date of Patent: May 28, 1996

[54] QUICK COUPLING DEVICE FOR DENTAL PROSTHESIS

[75] Inventors: Ezio Nardi; Gianni Storni, both of Bologna, Italy

[73] Assignee: Rhein 83 S.N.C. Di Nardi Ezio & C. Zago, 10, Bologna, Italy

[21] Appl. No.: 289,617

[22] Filed: Aug. 11, 1994

Related U.S. Application Data

[63] Continuation-in-part of Ser. No. 74,624, Jun. 11, 1993, abandoned.

[30] Foreign Application Priority Data

Jun. 19, 1992 [IT] Italy .................... BO920133 U

[51] Int. Cl.⁶ .................... A61C 13/12; A61C 13/225; A61C 8/00
[52] U.S. Cl. .................... 433/172; 433/173
[58] Field of Search .................... 433/167, 172, 433/173, 174, 175, 176, 181, 182

[56] References Cited

U.S. PATENT DOCUMENTS

| | | | |
|---|---|---|---|
| 3,579,831 | 5/1971 | Stevens | 433/174 |
| 3,732,621 | 5/1973 | Bostrom | 433/174 |
| 4,907,969 | 3/1990 | Ward | 433/174 X |
| 5,194,000 | 3/1993 | Dury | 433/173 |
| 5,211,561 | 5/1993 | Graub | 433/172 X |
| 5,215,460 | 6/1993 | Perry | 433/173 X |

FOREIGN PATENT DOCUMENTS

370865  9/1963  Switzerland .................... 433/172

*Primary Examiner*—Nicholas D. Lucchesi

[57] ABSTRACT

Quick coupling device for a dental prostheses including: a substantially spherical male element, monolithically associable with a fixed part of the prosthesis for protruding from a gingival region; a connecting element having a hollow seat for coupling to the male element and externally provided with a spherical surface; a female element, shaped complementarily to the external spherical surface of the connecting element, correspondingly provided on a removable part of the prosthesis and coupleable to the connecting element.

27 Claims, 7 Drawing Sheets

QUICK COUPLING DEVICE FOR DENTAL PROSTHESIS

This application is a continuation-in-part of application Ser. No. 08/074,624, filed Jun. 11, 1993, now abandoned.

BACKGROUND OF THE INVENTION

The present invention relates to a quick coupling device for dental prostheses.

As is known, removable dental prostheses provided with appropriate couplings for quick anchoring to residual dental structures are currently available.

In particular, Italian utility model patent no. 211276 discloses a quick coupling capable of ensuring durable engagement. This known coupling has a spherical male element and a female element which is shaped complementarily to said male element and is shaped so as to form a sort of small cap of plastic material which is accommodatable and stably retainable in the removable part of the prosthesis.

Conveniently, the seat of said plastic cap is formed in a metallic part which is monolithic with the removable part of the prosthesis. Said metallic part is preferably obtained by lost-wax casting of the dental arch to be restored starting from a model, made of refractory material.

The male element is supported by a metallic pin adapted to be cemented inside a dental root and prefabricated or obtained by casting from an element made of calcinable plastic material.

Couplings constituted by a tubular dental implant destined to become monolithic with the fixed part of the prosthesis are also known; a stem of said male element is inserted and screwed into said tubular implant.

The male elements also act as references for the correct fitting of the removable part of the prosthesis. However, in the manufacture of the prosthesis there are often considerable problems in ensuring a correct parallel arrangement of said male elements, as is necessary for the optimum functionality of said prosthesis.

SUMMARY OF THE INVENTION

An aim of the present invention is to solve the above problem by providing a device which allows to provide quick couplings for dental prostheses which can ensure the correct parallel arrangement of said couplings.

Within the scope of this aim, an object of the present invention is to provide a device for manufacturing quick couplings for dental prostheses which are simple in concept, safe and reliable in operation and versatile in use.

The above aim and object, and other aims and advantages which will become apparent hereinafter are achieved, according to the present invention, by a quick coupling device for dental prostheses, characterized in that it comprises: a substantially spherical male element, monolithically associable with a fixed part of the prosthesis for protruding from a gingival region; a connecting element, having a hollow seat for coupling to said male element and externally provided with a spherical surface; a female element, shaped complementarily to said external spherical surface of said connecting element, correspondingly provided on a removable part of the prosthesis and coupleable to said connecting element.

BRIEF DESCRIPTION OF THE DRAWINGS

The details of the invention will become apparent from the following detailed description of a preferred embodiment of the quick coupling device for dental prostheses, illustrated only by way of non-limitative example in the accompanying drawings, wherein.

DESCRIPTION OF THE PREFERRED EMBODIMENTS

Initially with particular reference to FIGS. 1, 2, 3 and 4, the quick coupling for dental prostheses has a substantially spherical male element 1, which extends from an intraradicular pin 2 which can be cemented inside a dental root; actually, the spherical element 1 has a flattened portion 1a located at the base which connects it to a narrower neck portion 2a of the pin 2.

Figure 1:
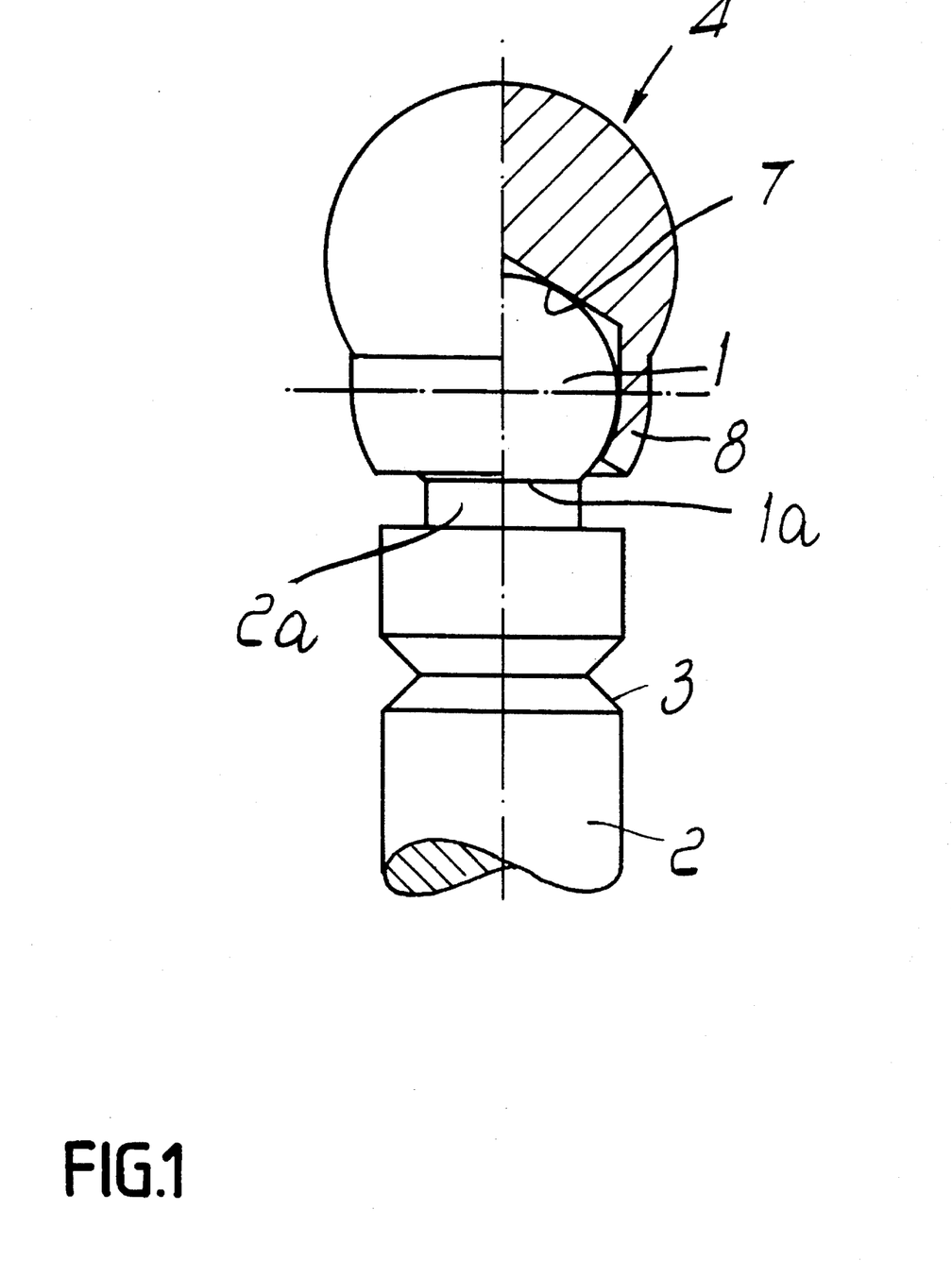
FIG. 1 is a partially cutout sectional side view of the device according to the present invention.

In order to provide a more stable connection, the pin 2, which has a conical profile, is provided with a plurality of uniformly spaced annular grooves 3 having a triangular cross-section.

Preferably, the male element 1, together with the related pin 2, is made of titanium or of high-strength ceramic material.

The male element 1 is coupleable, by interposing a connecting element 4, to a female element 5 located in a cavity seat 13 in the gingival region of a removable part of the prosthesis P.

Said female element 5 is defined by a sort of cap 6 made of a resilient plastic material, which is accommodatable and stably retainable in the removable part of the prosthesis. In practice, in fact, the cap 6 is externally provided with a shoulder 6a, and the corresponding cavity seat 13 of the prosthesis is shaped complementarily with respect to its external surface. Furthermore, the seat 13 for the cap 6 is preferably formed in a metallic part having an internal surface shaped complementarily to the outer surface of said cap. The cap couples to the seat with a snap-together action without the possibility of disengaging it, except by destroying it.

Said metallic part is conveniently constituted by a cap which is prefabricated or obtained by casting. In this second case, the metallic cap can be produced monolithically with a bar-like element of the type shown in U.S. patent application Ser. No. 07/883,435. Said element is produced starting from a pair of auxiliary bars, made of calcinable material, which are coupleable on top of each other and form, in corresponding positions, respective annular portions which cooperate to form a recess shaped complementarily to the plastic cap 6.

According to the different requirements, in practice one uses multiple portions of said calcinable bars, joined by means of wax or the like so as to obtain a model which allows to produce, by lost-wax casting, a metallic part destined to be monolithically associated with the removable part of the prosthesis.

As shown in detail in FIG. 1, the connecting element 4 has a sperical hollow seat 7 for movably coupling to the male element 1, and is externally provided with a spherical surface which is complementary to the internal surface of the cap 6. The hollow seat 7 is surrounded by a lip 8 which is conveniently deformable after the insertion of the male element 1 so as prevent subsequent extraction of said male element 1.

As clearly appears from FIG. 1, the spherical element 1 connected by the neck portion 2a to the pin 2 comprises an upper hemispherical portion and lower hemispherical portion separated by an equatorial plane at the level of the horizontal axis shown in the figure. The lower hemispherical portion is connected at a lowest area thereof by the neck portion 2a to the pin element 2. The substantially spherical hollow seat 7 of the connecting element 4, is shown also to comprise un upper portion for enclosing said upper hemispherical portion of the male element 1 and a lower portion extending under said equatorial plane of the male element 1. Such lower portion of the seat 7 is constituted by the lip element 8, which is snugly fitting around an area of said lower hemispherical portion of the male element 1 which is situated immediately under said equatorial plane. The downwardly extending lip 8 leaves free in this way the lower portion of said lower hemispherical portion which extends around said neck element 2a. Accordingly, the connecting element is allowed to freely tilt with respect to the longitudinal axis of the pin element 2.

Figure 2:
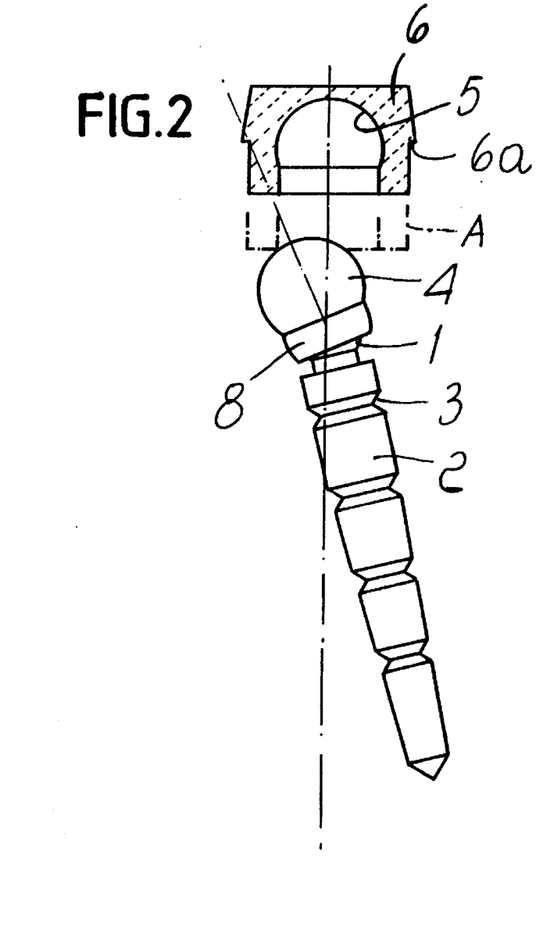
FIGS. 2, 3 and 4 are respective side views of said device during successive steps of assembly.
Figure 3:
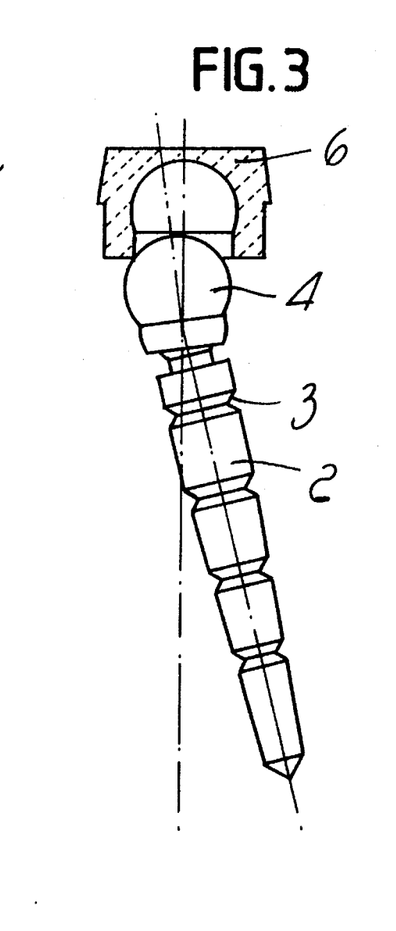
Figure 4:
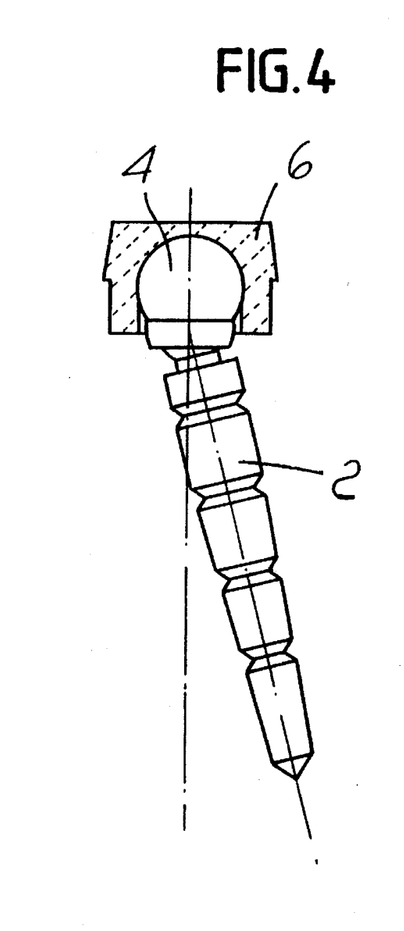

In practice, the cap 6, rigidly associated with the removable part of the prosthesis, is placed on the spherical surface of the connecting element 4 to which it couples by means of the female element complementarily shaped inner surface, as shown by the dashed line A in FIG. 2. By virtue of the coupling, which allows a certain degree of rotation with respect to the male element 1, the connecting element 4 performs an angular rotation with respect to the axis of the pin 2 so as to find exact reference with respect to the cap 6 (FIG. 3). This exact reference is thus obtained automatically during coupling, accordingly ensuring the parallel arrangement of the couplings (FIG. 4).

Figure 5:
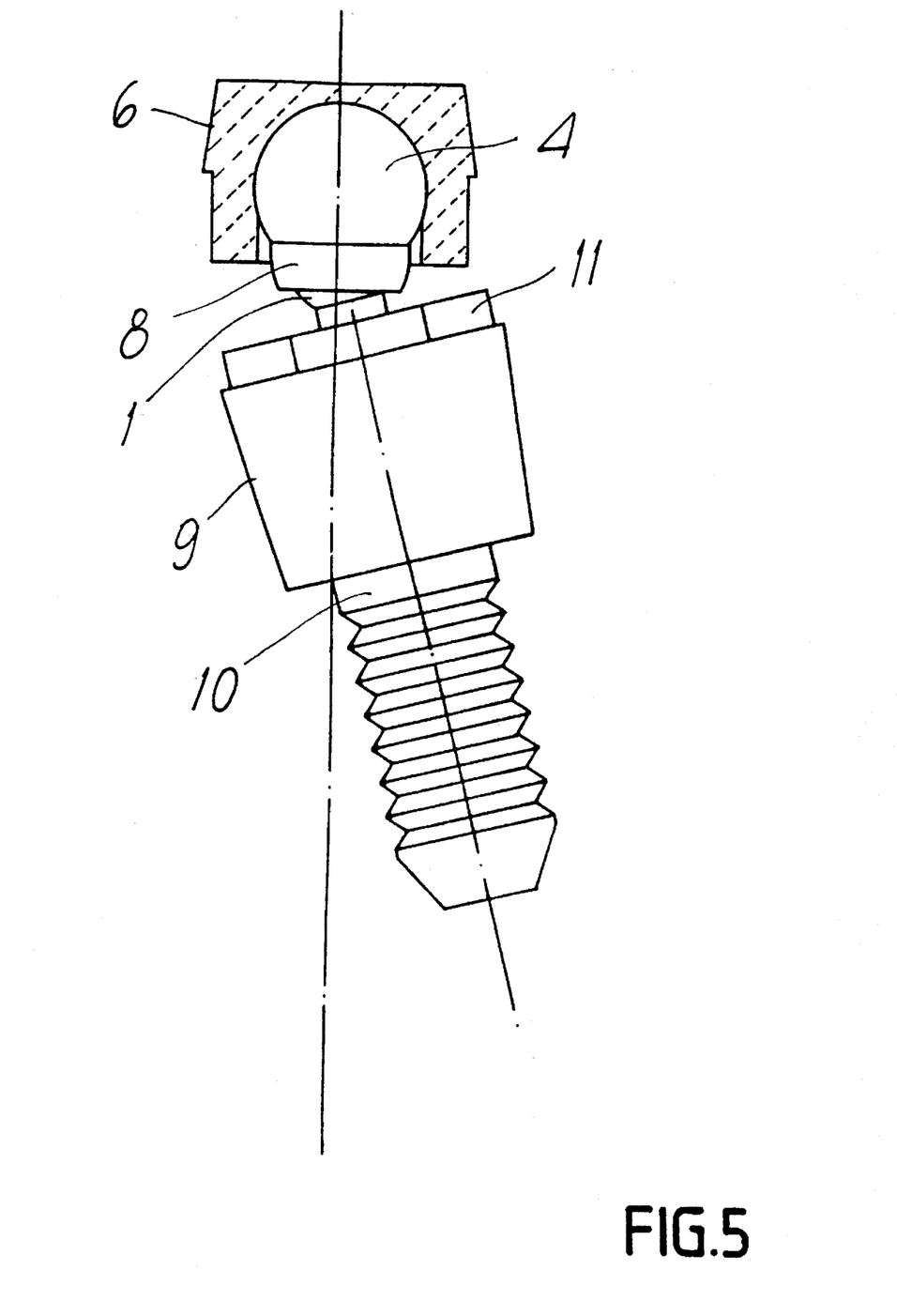
FIG. 5 is a side view of the device applied to a dental implant coupling.
Figure 11:
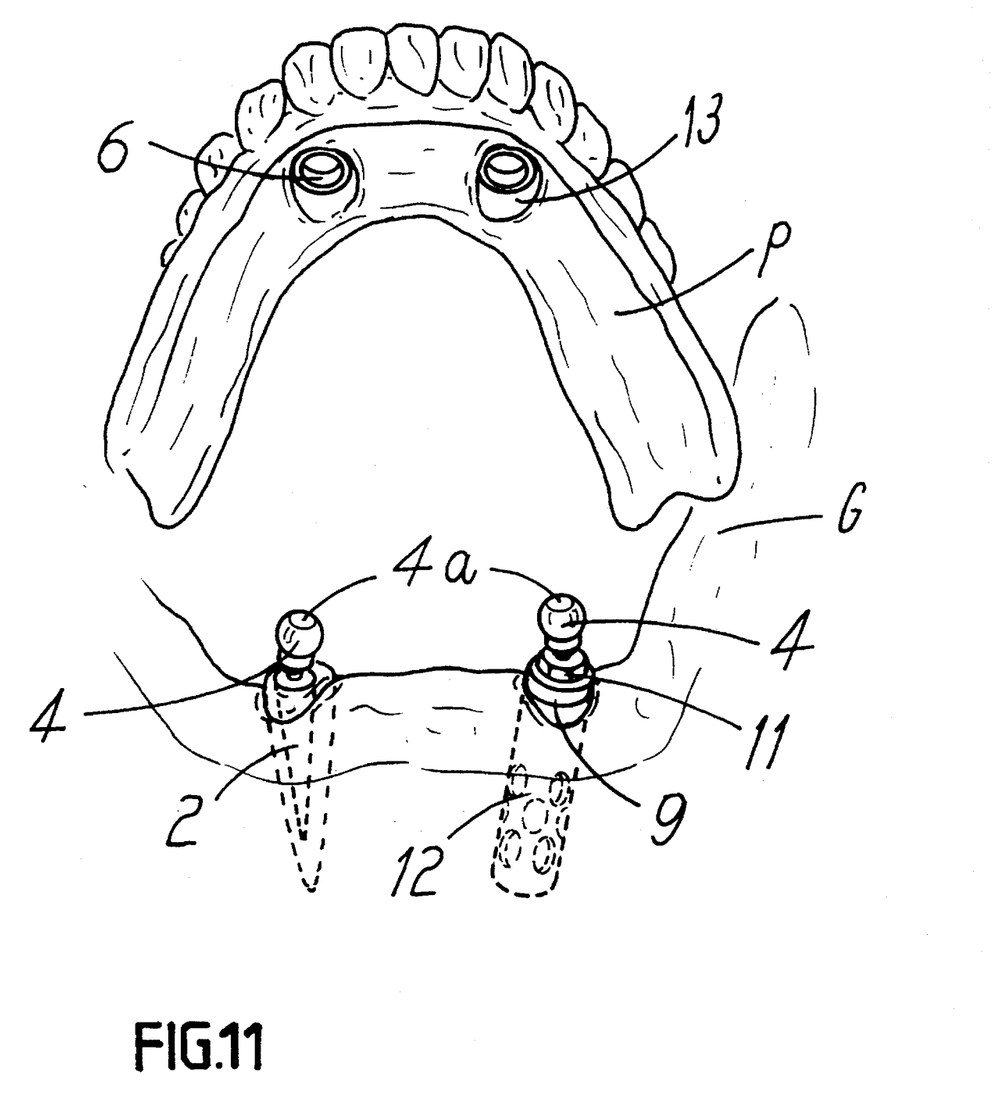
FIG. 11 is a perspective view of the fixed and removable parts of the prosthesis shown in the ready-to-assemble configuration.

In the embodiment shown in FIG. 5, the male element 1 extends from a frustum-shaped body 9, the larger flat surface whereof is adjacent to said male element 1. The body 9 extends axially into a threaded cylindrical stem 10 screwed into a conventional tubular dental implant 12 which is shown in FIG. 11; said implant, also known as an insert, is monolithically associated with the fixed part of the prosthesis in the gum 6 (FIG. 11).

In order to screw the threaded stem 10 in the insert 12, the body 9 forms, at its larger flat surface, a hexagonal nut 11 which is engageable by an appropriate wrench. As an alternative, it is possible to provide, in diametrically opposite positions, a pair of notches which are engageable by means of an appropriate tool.

The threaded stem 10 is appropriately shaped and dimensioned in relation to the corresponding dental insert. The stem 10 is screwed fully into said insert; the frustum-shaped body 9 passes through the uletic or gingival region, from which the spherical element 1 protrudes.

Figure 6:
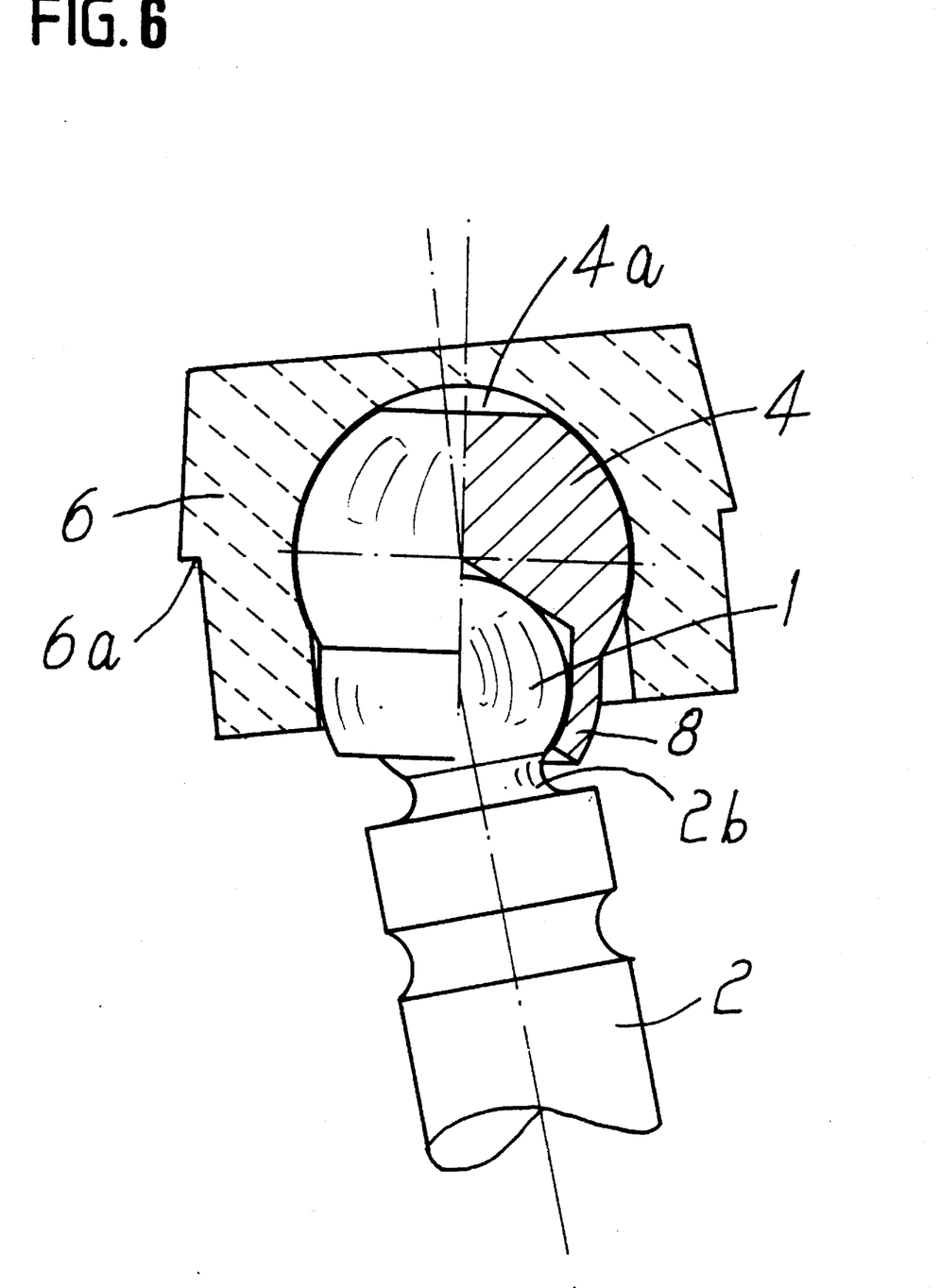
FIG. 6 is a partial cutout sectional side view of a modified embodiment of the device according to the invention shown in its assembled configuration.
Figure 7:
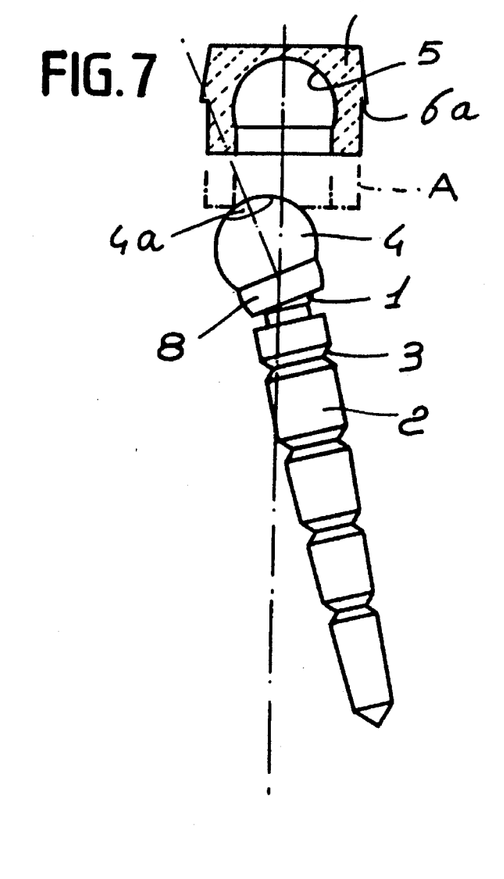
FIGS. 7, 8 and 9 are respective side views of said modified embodiment of the device during successive steps of assembly.
Figure 8:
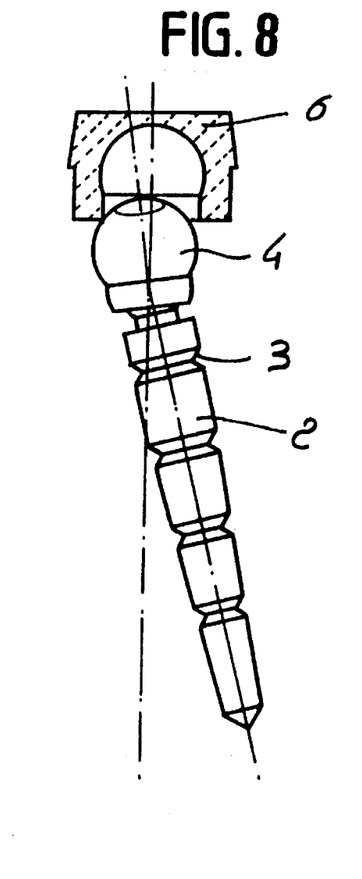
Figure 9:
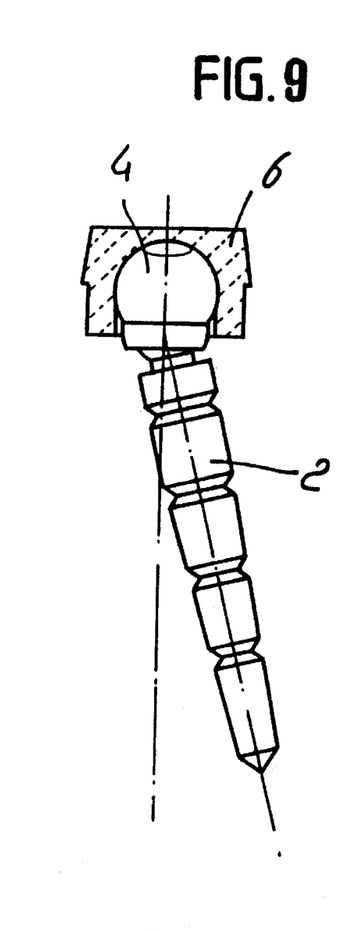
Figure 10:
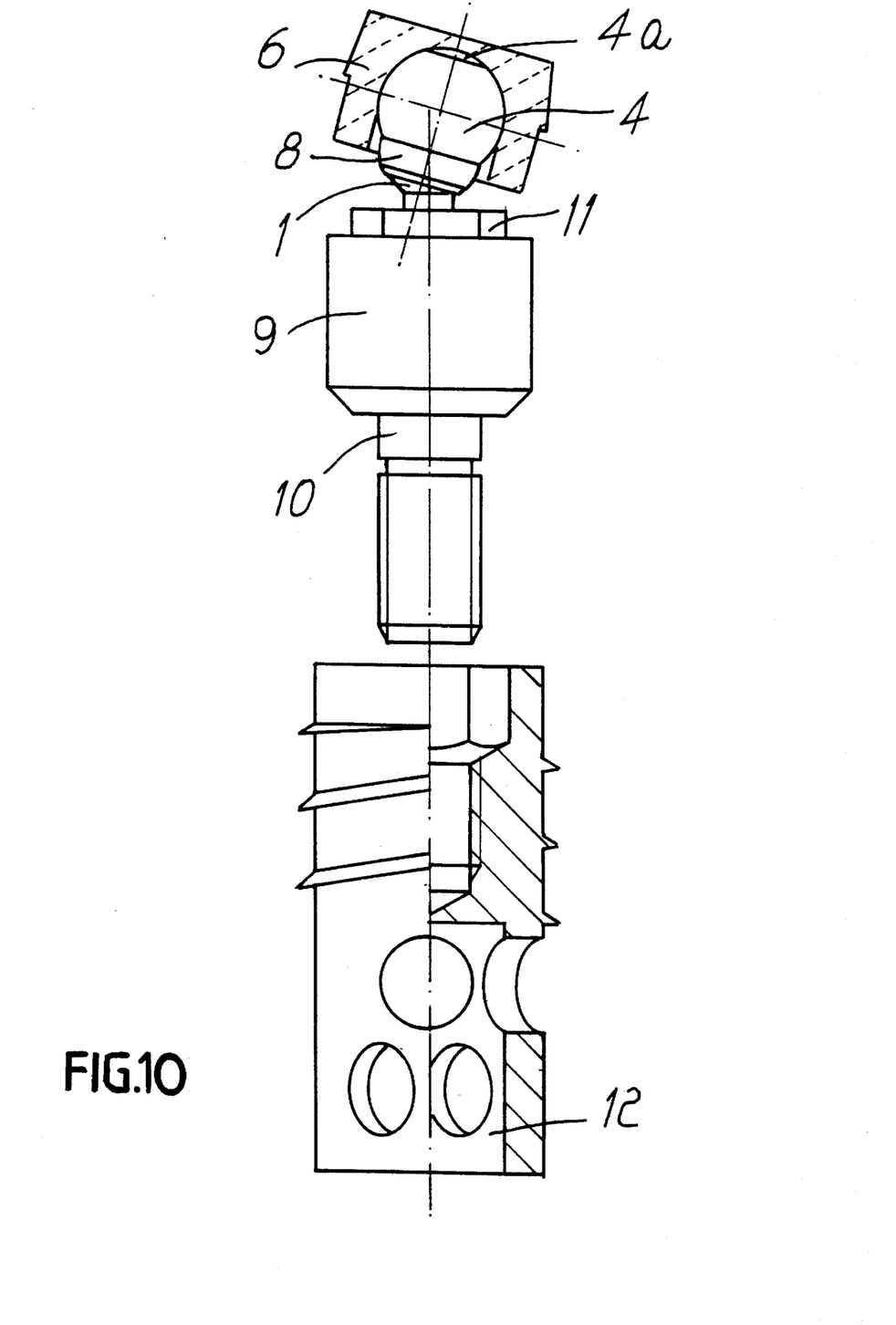
FIG. 10 is a side view of the modified embodiment of the device applied to a dental implant coupling and of the relative tubular dental implant.

A modified embodiment of the device according to the invention is shown in FIG. 6 where the male element 1 is connected to the pin 2 by means of a narrower neck portion having a recessing 2b thereabout. Such neck recessing 2b allows the connecting element to tilt even more increasing the overall capacity of the coupling to adapt to any particular situation of a patient needing a prosthesis.

A general trend in the art is that the dental coupling devices should be fixed, since it is generally believed that a movable, not steady coupling could harm the patient's gum and anyway can provoke unpleasant sensations or even distress during chewing. Unexpectedly, it has been verified in practice that the coupling according to the present invention not only does not bother the patient in any manner, but has also a surprisingly benefic effect on his gingival tissue and helps consolidate shaky dental roots. It is believed that such benefic effect is induced exactly by the mobility of the coupling which favours a massaging action of the removable part of the prosthesis on the gum. The massaging action seems to be more efficient if the cap element 6 is made of a resilient plastic material which has a damping effect attenuating the chewing stresses and shocks discharged on the coupling and the gum.

The practice further showed that the damping effect and the massaging effect are even more enhanced by providing at an upper region of the spherical surface of the connecting element 4, a flat region 4a as shown in the FIGS. 6–11. In this way between the flat region 4a of the connecting element and the inner surface of the female element 5 a cavity is created which allows the cap 6 to elastically flex inwardly and acting like compression spring.

A similar shock-absorbing structure with a flat region provided in an upper region of a male element, which however is connected directly to a resilient material cap, without the interposition of a tiltable connecting element, has been already disclosed in the prior patent U.S. Pat. No. 5,030,094 issued to the same applicant. The coupling device of the prior document, though efficient for absorbing shocks, has not shown any evident beneficial effect on the gums or the dental roots of the patient.

In conclusion, the described device allows to provide quick couplings for dental prostheses which ensure the correct parallel arrangement of said couplings. The device furthermore ensures the safe and durable holding of the couplings between the male elements 1 and the caps 6, without limiting the possibility of removing the movable part of the prosthesis.

Last but not least, is the benefic effect which the device according to the invention has proved to have on the health of the patient's gum.

In the practical embodiment of the device according to the present invention, the materials employed, as well as the shapes and dimensions, may be any according to the requirements.

We claim:

1. Quick coupling device for a dental prosthesis having a removable part, a cavity seat being provided in said removable part and a fixed part coupleable at a gingival region, said device comprising:

a pin element, defining a longitudinal axis thereof and being monolithically associatable with said fixed part;

a substantially spherical male element extending from said pin element for protruding from said gingival region, said male element comprising an upper hemispherical portion and a lower hemispherical portion, said upper and said lower hemispherical portions being separated by an equatorial plane, and said lower hemispherical portion being connected at a lowest area thereof by a neck portion to said pin element;

a connecting element having an external spherical surface and a spherical hollow seat, said spherical hollow seat having un upper portion enclosing said upper hemispherical portion of said male element and a lower portion extending under said equatorial plane of said male element, said lower portion being constituted by a lip element snugly fitting around an area of said lower hemispherical portion situated immediately under said equatorial plane of said male element, so as to leave free a lower portion of said lower hemispherical portion, said free lower portion extending around said neck element, said connecting element being allowed to freely tilt with respect to said longitudinal axis of said pin element;

a female element having an inner surface being shaped complementarily to said external spherical surface of said connecting element for being coupleable to said connecting element, and an external surface being correspondingly adapted to be accommodated in said cavity seat provided in said removable part;

whereby automatic exact reference between said female element, and said pin element is obtained during coupling of said female element on said connecting element.

2. Device according to claim 1, wherein said neck portion has a recessing thereabout for allowing said connecting element to tilt to a higher inclination with respect to said longitudinal axis of said pin element.

3. Device according to claim 1, wherein said lip is deformable upon insertion of said male element, so as to snugly fit around said male element and to prevent subsequent extraction of said male element.

4. Device according to claim 1, wherein said male element protrudes from a body which extends axially into a threaded cylindrical stem being suitable to be screwed into a tubular dental implant which is adapted to be monolithic with said fixed part of the prosthesis.

5. Device according to claim 4, wherein said body has a frustum-shaped portion comprising a larger flat surface, said larger flat surface being adjacent to said male element, said body further having, at said larger flat surface thereof, a profile adapted to be engaged by appropriate screw-coupling means.

6. Device according to claim 1, wherein said pin element has a conical profile and is provided with a plurality of uniformly spaced annular grooves whereby being suitable to be cemented inside a dental root for constituting said fixed part.

7. Device according to claim 1, wherein said male element and said pin element are monolithically associated and made of a material selected from titanium and high-strength ceramic material.

8. Device according to claim 1, wherein said female element is provided on said external surface thereof with a shoulder for being received in a correspondingly shaped seat comprised in said cavity of said removable part.

9. Device according to claim 8, wherein said female element is made of plastic material, said seat in said removable part being formed in metal, thereby said female element being coupleable to said seat by a snap-together action.

10. Quick coupling device for a dental prosthesis having a removable part, a cavity seat being provided in said removable part and a fixed part coupleable at a gingival region, said device comprising:

a pin element, defining a longitudinal axis thereof and being monolithically associatable with said fixed part;

a substantially spherical male element extending from said pin element for protruding from said gingival region, said male element comprising an upper hemispherical portion and lower hemispherical portion, said upper and said lower hemispherical portions being separated by an equatorial plane, and said lower hemispherical portion being connected at a lowest area thereof by a neck portion to said pin element;

a connecting element having a spherical hollow seat, said spherical hollow seat having un upper portion to enclose said upper hemispherical portion of said male element and a lower portion extending under said equatorial plane of said male element, said lower portion being constituted by a lip element snugly fitting around an area of said lower hemispherical portion situated immediately under said equatorial plane of said male element, so as to leave free a lower portion of said lower hemispherical portion, said free lower portion extending around said neck element, said connecting element being allowed to freely tilt with respect to said longitudinal axis of said pin element;

a female element having an inner surface being shaped complementarily to said external spherical surface of said connecting element for being coupleable to said connecting element, and an external surface being correspondingly adapted to be accommodated in said cavity provided in said removable part, said female element being made of a resilient plastic material.

11. Device according to claim 10, wherein said neck portion has a recess thereabout for allowing said connecting element to tilt to a higher inclination with respect to said longitudinal axis of said pin element.

12. Device according to claim 10, wherein said lip is deformable upon insertion of said male element, so as to snugly fit around said male element and to prevent subsequent extraction of said male element.

13. Device according to claim 10, wherein said male element protrudes from a body which extends axially into a threaded cylindrical stem being suitable to be screwed into a tubular dental implant which is adapted to be monolithic with said fixed part of the prosthesis, said body and said cylindrical stem constituting said pin element.

14. Device according to claim 13, wherein said body has a frustum-shaped portion comprising a larger flat surface, said larger flat surface being adjacent to said male element, said body further having, at said larger flat surface thereof, a profile adapted to be engaged by appropriate screw-coupling means.

15. Device according to claim 10, wherein said pin element has a conical profile and is provided with a plurality of uniformly spaced annular grooves whereby being suitable to be cemented inside a dental root for constituting said fixed part.

16. Device according to claim 10, wherein said male element and said pin element are monolithically associated and made of a material selected from titanium and high-strength ceramic.

17. Device according to claim 10, wherein said female element is provided on said external surface thereof with a shoulder for being received in a correspondingly shaped seat comprised in said cavity of said removable part.

18. Device according to claim 17, wherein said seat in said removable part is formed in metal, said female element being coupleable to said seat by a snap-together action.

19. In a quick coupling device for a dental prosthesis having a removable part, a cavity seat being provided in said removable part and a fixed part coupleable at a gingival region, said device comprising:

a pin element, defining a longitudinal axis thereof and being monolithically associatable with said fixed part;

a substantially spherical male element extending from said pin element for protruding from said gingival region, said male element comprising an upper hemispherical portion and a lower hemispherical portion, said upper and said lower hemispherical portions being separated by an equatorial plane, and said lower hemispherical portion being connected at a lowest area thereof by a neck portion to said pin element;

a connecting element having an external spherical surface and a spherical hollow seat, said spherical hollow seat having un upper portion to enclose said upper hemispherical portion of said male element and a lower portion extending under said equatorial plane of said male element, said lower portion being constituted by a lip element snugly fitting around an area of said lower hemispherical portion situated immediately under said equatorial plane of said male element, so as to leave free a lover portion of said lower hemispherical portion, said free lower portion extending around said neck element, said connecting element being allowed to freely tilt with respect to said longitudinal axis of said pin element;

a female element having an inner surface being shaped complementarily to said external spherical surface of said connecting element for being coupleable to said connecting element, and an external surface being correspondingly adapted to be accommodated in said cavity seat provided in said removable part; said female element being made of a resilient plastic material;

wherein said spherical surface of said connecting element has at an upper region thereof a flat region, a cavity being defined between said flat region of said connecting element and said inner surface of said female element.

20. In a quick coupling device for a dental prosthesis, a male element connected to a pin element according to claim 19, wherein said neck portion has a recess thereabout for allowing said connecting element to tilt to a higher inclination with respect to said longitudinal axis of said pin element.

21. In a quick coupling device for a dental prosthesis a connecting element according to claim 19, wherein said lip element is deformable upon insertion of said male element, so as to snugly fit around said male element and to prevent subsequent extraction of said male element.

22. In a quick coupling device for a dental prosthesis a male element according to claim 19, wherein a body, from which said male element protrudes, extends axially into a threaded cylindrical stem, said stem being suitable to be screwed into a tubular dental implant, said tubular dental implant being adapted to be monolithic with said fixed part of the prosthesis.

23. In a quick coupling device for a dental prosthesis a male element according to claim 22, wherein said body has a frustum-shaped portion comprising a larger flat surface, said larger flat surface being adjacent to said male element, said body further having, at said larger flat surface thereof, a profile adapted to be engaged by appropriate screw-coupling means.

24. In a quick coupling device for a dental prosthesis a male element connected to a pin element according to claim 19, wherein said pin element has a conical profile and is provided with a plurality of uniformly spaced annular grooves whereby being suitable to be cemented inside a dental root for constituting said fixed part.

25. In a quick coupling device for a dental prosthesis a male element and a pin element according to claim 19, wherein said male element and said pin element are monolithically associated and made of a material selected from titanium and high-strength ceramic.

26. In a quick coupling device for a dental prosthesis a female element according to claim 19, wherein a shoulder is provided on said external surface of said female element, said shoulder being adapted for being received in a correspondingly shaped seat comprised in said cavity of said removable part.

27. In a quick coupling device for a dental prosthesis a cavity seat according to claim 19, wherein said seat in said removable part is formed in metal, said female element being coupleable to said seat by a snap-together action.

* * * * *